United States Patent
Bharat et al.

(10) Patent No.: US 10,080,910 B2
(45) Date of Patent: Sep. 25, 2018

(54) REAL-TIME ADAPTIVE DOSE COMPUTATION RADIATION THERAPY

(71) Applicant: KONINKLIJKE PHILIPS N.V., Eindhoven (NL)

(72) Inventors: Shyam Bharat, Cortlandt Manor, NY (US); Vijay Parthasarathy, Mt. Kisco, NY (US); Ameet Kumar Jain, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 269 days.

(21) Appl. No.: 14/649,559

(22) PCT Filed: Sep. 17, 2013

(86) PCT No.: PCT/IB2013/058588
§ 371 (c)(1),
(2) Date: Jun. 4, 2015

(87) PCT Pub. No.: WO2014/096993
PCT Pub. Date: Jun. 26, 2014

(65) Prior Publication Data
US 2015/0306423 A1 Oct. 29, 2015

Related U.S. Application Data

(60) Provisional application No. 61/737,880, filed on Dec. 17, 2012.

(51) Int. Cl.
*A61N 5/10* (2006.01)
*A61B 6/03* (2006.01)
(Continued)

(52) U.S. Cl.
CPC ............ *A61N 5/1031* (2013.01); *A61B 6/032* (2013.01); *A61B 6/5247* (2013.01); *A61B 8/08* (2013.01);
(Continued)

(58) Field of Classification Search
CPC ........................... A61B 19/5244; A61B 19/52
See application file for complete search history.

(56) References Cited

U.S. PATENT DOCUMENTS 5,505,932 A * 4/1996 Grinstaff .......... A61K 47/48853
424/9.3
5,769,790 A 6/1998 Watkins et al.
(Continued)

FOREIGN PATENT DOCUMENTS

JP 2003117010 4/2003
WO 03039370 A1 5/2003
(Continued)

OTHER PUBLICATIONS

Schlosser, J., et al.; Telerobotic system concept for real-time soft-tissue imaging during radiotherapy beam delivery; 2010; Med. Phys.; 37(12)6357-6367.

*Primary Examiner* — Hien Nguyen

(57) ABSTRACT

A radiation therapy system (1) includes an ultrasound (US) imaging unit (2), a registration unit (30), an US motion unit (44), and a real-time dose computation engine (46). The ultrasound (US) imaging unit (2) generates a baseline and real-time US images (3) of a subject body (4) region including a target and one or more Organs At Risk (OARs). The registration unit (30) deformably registers a planning image (32) and the baseline US image (36), and maps (66) radiation absorptive properties of tissue in the planning image (32) to the baseline US image (36). The US motion unit (44) measures motion of the target volume and OARs during radiation therapy treatment based on the real-time US
(Continued)

Figure 1:
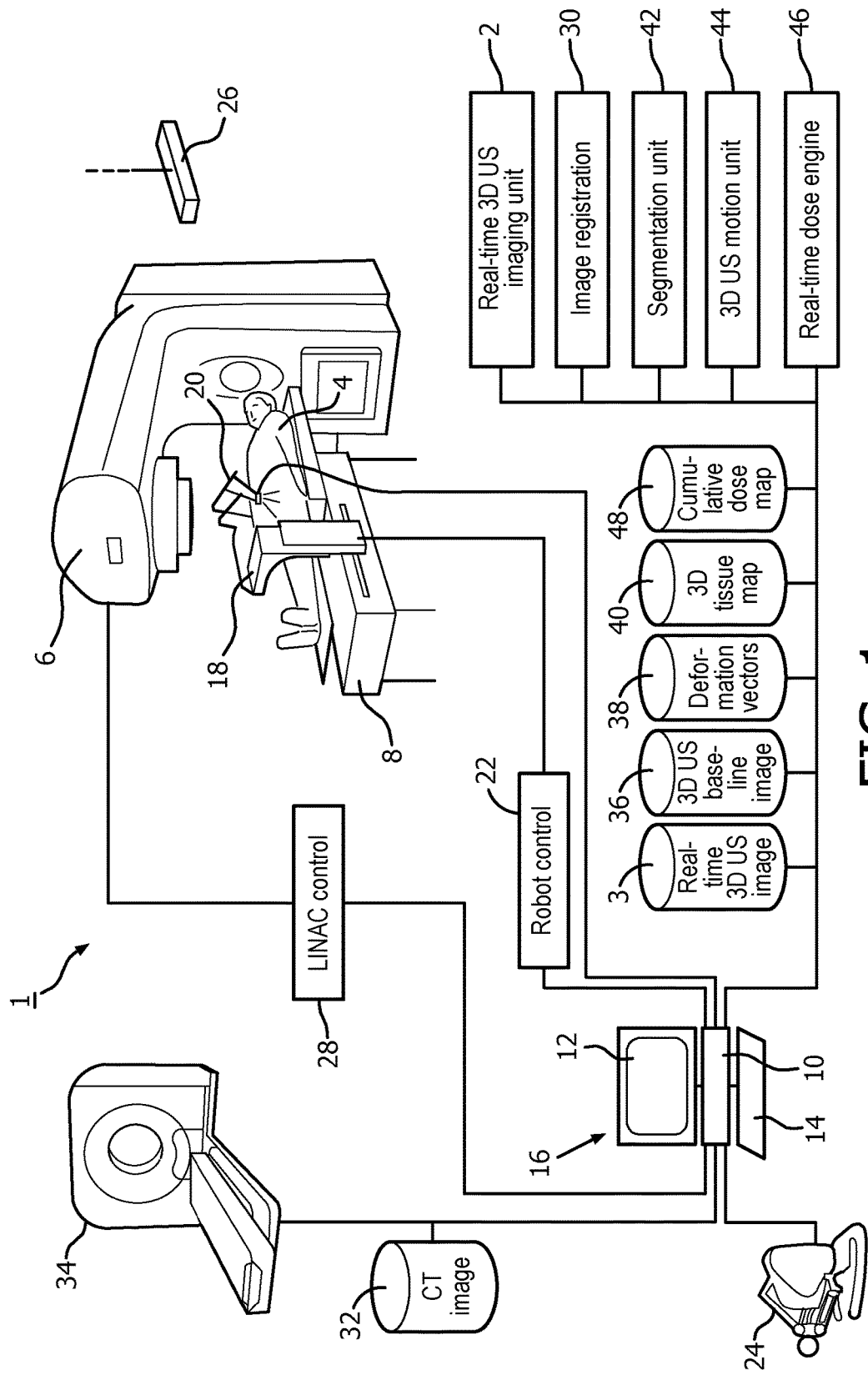

images. The real-time dose computation engine (46) computes a real-time radiation dose delivered to the tissues based on the tissue radiation absorptive properties mapped from the baseline or planning images to the real-time 3D US images (3).

15 Claims, 2 Drawing Sheets

(51) Int. Cl.
  *A61B 6/00* (2006.01)
  *A61B 8/08* (2006.01)
  *A61B 8/00* (2006.01)
  *A61B 34/30* (2016.01)

(52) U.S. Cl.
  CPC .......... *A61B 8/4218* (2013.01); *A61B 8/4444* (2013.01); *A61B 8/463* (2013.01); *A61B 8/483* (2013.01); *A61B 34/30* (2016.02); *A61N 5/1037* (2013.01); *A61N 5/1039* (2013.01); *A61N 5/1048* (2013.01); *A61N 5/1049* (2013.01); *A61N 5/1067* (2013.01); *A61N 5/1071* (2013.01); *A61N 5/1077* (2013.01); *A61N 2005/1058* (2013.01); *A61N 2005/1072* (2013.01); *A61N 2005/1074* (2013.01)

(56) References Cited

U.S. PATENT DOCUMENTS

| | | | |
|---|---|---|---|
| 2007/0014446 A1* | 1/2007 | Sumanaweera | G06T 15/08 382/128 |
| 2008/0002811 A1 | 1/2008 | Allison | |
| 2012/0035462 A1 | 2/2012 | Maurer, Jr. et al. | |

FOREIGN PATENT DOCUMENTS

| | | |
|---|---|---|
| WO | 2007002926 A2 | 1/2007 |
| WO | 2009012577 A1 | 1/2009 |
| WO | 2012069965 A1 | 5/2012 |
| WO | 2012080949 A1 | 6/2012 |
| WO | 2013179221 A1 | 12/2013 |

* cited by examiner

REAL-TIME ADAPTIVE DOSE COMPUTATION RADIATION THERAPY

CROSS REFERENCE TO RELATED APPLICATIONS

This application is a national filing of PCT application Ser. No. PCT/IB2013/058588, filed Sep. 17, 2013, published as WO 2014/096993 A1 on Jun. 26, 2014, which claims the benefit of U.S. provisional application Ser. No. 61/737,880 filed Dec. 17, 2012, which is incorporated herein by reference.

The following relates generally to radiation therapy and medical imaging. It finds particular application in conjunction with radiation therapy real-time dose computation and three dimensional real-time ultrasound imaging, and will be described with particular reference thereto. However, it will be understood that it also finds application in other usage scenarios and is not necessarily limited to the aforementioned application.

Radiation therapy (RT) identifies and delivers radiation to kill cancerous cells in a target area while preserving normal cells which surround the target area and include organs at risk (OARs). The planning process for RT plans delivery of radiation in fractionated doses or doses over time. The fractionated treatments improve the destruction rate of cancerous cells and allow normal cells to recover. The planning process is a detailed process of determining the size, shape, direction, and duration of radiation beams to precisely deliver a maximum dose to the target area while minimizing exposure to OARs. The different tissue densities such as bones, soft tissues, and organ tissues in the path of each radiation beam are considered in the computation of a planned dose. Typically, a Computed Tomography (CT) X-ray image is used to evaluate the different tissue densities in the various radiation paths and provide attenuation information. CT images can provide high resolution and include contrasts corresponding to tissue densities.

The plan developed through RT planning is delivered during RT treatment using devices such as a linear accelerator (LINAC) to deliver beams of radiations from different directions of selected shapes and sizes for a timed duration. Recent improvements in RT delivery include identification of target areas during RT delivery with ultrasound (US). US uses high frequency sound waves to provide real-time images and the high frequency sound waves do not interfere with the concurrent radiation treatment beams or conversely the radiation beams do not interfere with the US imaging. The US probe or transducer which sends and receives the sound is held in position against a patient's body by a robotic arm. The US improves targeting by identifying the target internal to the patient's body relative to the projected path of any radiation beam. Other methods include using implanted fiducials such as seeds visible with US imaging, fluoroscopy or other real-time/on-board imaging in a prostate (or other target) to improve targeting. A healthcare practitioner monitors the projected path typically superimposed on the US or planning image and can discontinue the treatment or adjust the patient position by moving a patient support or couch holding the patient. Images are recorded and evaluated by the RT planning software and healthcare practitioner makes any adjustments in the next fractionated treatment.

However, patient tissues move during treatment delivery such as due to cardiac or respiratory motion. Patients sometimes cough, sneeze, or pass gas which can briefly modify the position of the target, surrounding tissues, and/or OARs, moving the target out of and the OARs into the path of the radiation beam, etc. Current techniques do not monitor or compute the actual dose delivered during RT treatment to the target area, surrounding tissues, OARs which means that healthy tissues can be overdosed or the targeted area underdosed in a fractionated treatment. No volumetric data is tracked during the treatment delivery. The analysis, dose computation, or evaluation is performed between fractionated treatments.

The following discloses a new and improved real-time adaptive dose computation in RT which addresses the above referenced issues, and others.

In accordance with one aspect, a radiation therapy system includes an ultrasound (US) imaging unit, a registration unit, an US motion unit, and a real-time dose computation engine. The ultrasound (US) imaging unit generates a baseline and real-time US images of a subject body region including a target and one or more Organs At Risk (OARs). The registration unit deformably registers a planning image and the baseline ultra-sound (US) image, and maps radiation absorptive properties of tissue in the planning image to the baseline US image. The US motion unit measures motion of the target volume and OARs during radiation therapy treatment based on the real-time US images. The real-time dose computation engine computes a real-time radiation dose delivered to the tissues based on the mapped tissue radiation absorptive properties and the real-time 3D US images.

In accordance with another aspect, a method of radiation therapy includes generating a baseline and real-time ultrasound (US) planning images of a subject body region including a target and one or more Organs-At-Risk (OARs). A planning image and the baseline 3D US image are deformably registered. Radiation absorptive properties of the tissue in the planning image are mapped to the baseline US image. The real-time motion of the target and organs at risk are measured during a radiation therapy treatment based on the real-time US images. A real-time radiation dose delivered to the tissues is computed based on the mapped tissue radiation absorptive properties and the real-time 3D US images.

In accordance with another aspect, a radiation therapy system includes a linear accelerator (LINAC), a robot-controlled ultrasound (US) imaging unit, a registration unit, an US motion unit, and a dose computation engine. The LINAC generates a plurality of beams of radiation into at least one targeted volume in a subject body, each beam of a size, shape, direction, strength, and duration based on a radiation treatment plan. The robot-controlled ultrasound (US) imaging unit generates 3-dimensional (3-D) US images of a region of the subject body which includes the at least one targeted volume, and surrounding tissues exposed to the plurality of beams of radiation delivered concurrently to and located relative to the 3-D US images. The registration unit deformably registers a computed tomography (CT) x-ray planning image and a baseline ultra-sound (US) images generated by the US unit prior to treatment, and maps tissue densities based on the CT planning image to the baseline 3D US images to generate a 3D tissue density map. The US motion unit measures motion of the targeted volume and surrounding tissues and registers the 3D tissue density map to the real time 3D US images generated by the US imaging unit. The dose computation engine computes a real-time radiation dose delivered to the at least one targeted volume, organs at risk and surrounding tissues based on the 3D tissue density map, the real-time US images, and the measured motion.

One advantage is that a real-time radiation dose during delivery of radiation is computed.

Another advantage resides in actions that can be taken during RT delivery based on the delivered dose.

Another advantage resides in a measurement on a voxel by voxel basis of real-time radiation dose of the target area, surrounding tissues, and OARs.

Another advantage resides in the real-time radiation dose measurement for the different tissues.

Another advantage resides in real time adjustment of the RT plan.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of a real-time adaptive dose computation RT system.

Figure 2:
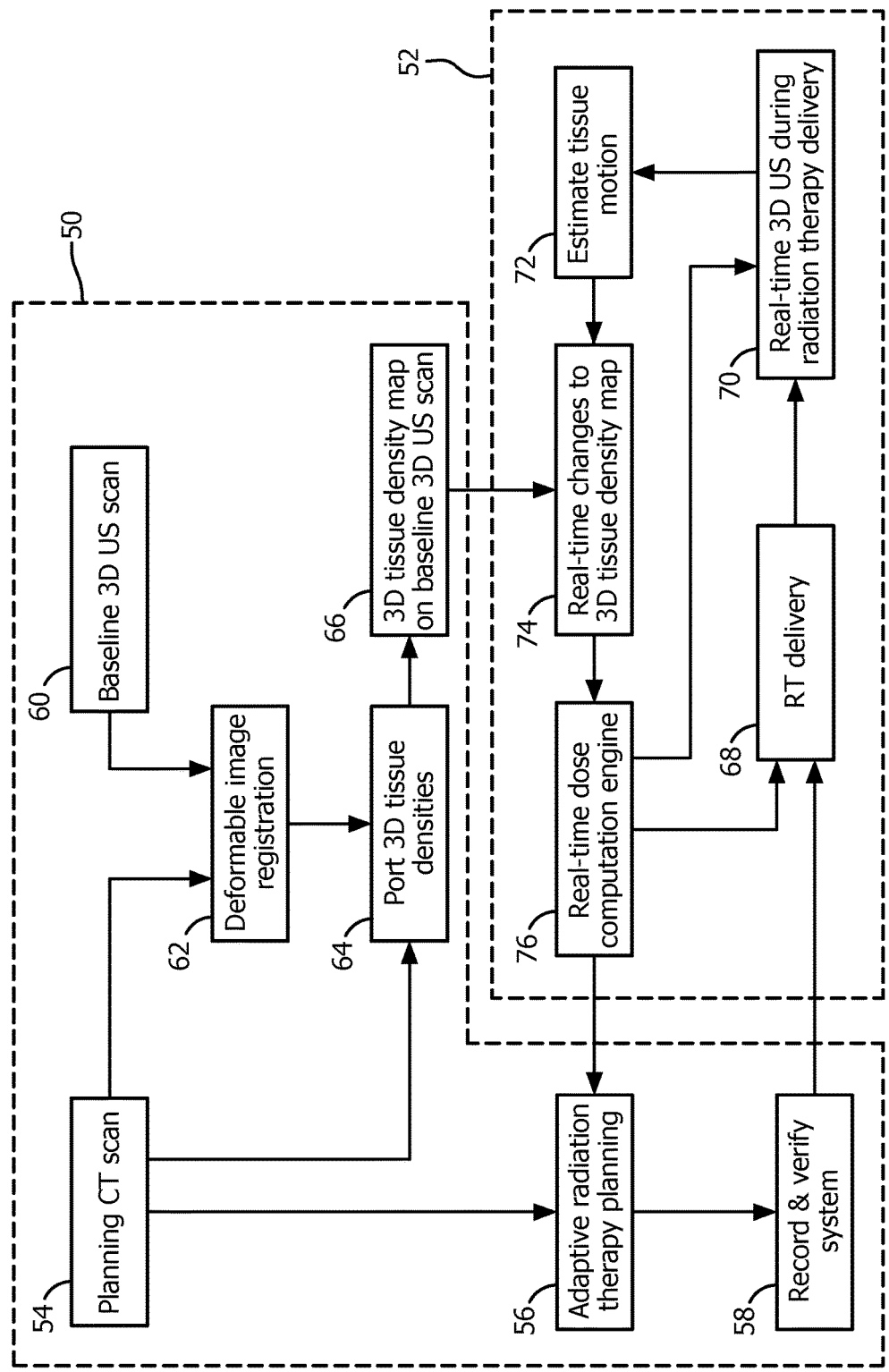

FIG. 2 flowcharts one method of a real-time adaptive dose computation radiation therapy.

With reference to FIG. 1, an embodiment of a real-time adaptive dose computation RT system 1 is schematically illustrated. The system includes a real-time three dimensional (3D) imaging unit 2 such as ultrasound (US) imaging unit, fluoroscopy imaging device, and the like. The real-time 3D US imaging unit generates real-time 3D US images 3 of a subject body 4 region. The US images 3 of the subject body region include tissues to which radiation is delivered concurrently from a radiation source such as a linear accelerator (LINAC) 6. The US images 3 are stored in a memory which can include a processor memory, computer memory, or non-transitory memory such as disk storage. The tissues exposed to radiation are measured relative to the projected radiation beams while the subject is positioned on a subject support 8 such as a couch or bed.

The real-time 3D US unit 2 includes one or more processors 10, a display device 12, and at least one input device 14. The processor 10, the display device 12, and the input device 14 can embodied in a workstation 16, such as a console, operator interface, and the like. The workstation can be a single desktop computer, multiple desktop computers connected via a network, a server computer, a laptop, a tablet, a combination and the like. The processor can be a single processor or multi-processor. Each processor can be a single core or a multi-core processor. The input device can include a keyboard, a mouse, a microphone, and the like. The display device can include a computer monitor, a television screen, a touch screen, tactile electronic display, Cathode ray tube (CRT), Storage tube, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, Head-mounted display, and the like.

The real-time 3D US unit 2 includes a robotic manipulator 18 which manipulates a US probe 20 or transducer controlled by a computer controlled robotic control 22. The real-time 3D US unit 2 can include a haptic interface 24 for positioning of the US probe 20 through the robotic control 22. The real-time 3D US unit 2 includes one or more optical tracking devices 26 which track the position of the robotic manipulator, LINAC, and the subject body. The tracking device can include a laser, video, RF tracker, or electro-mechanical feedback devices on the LINAC's gantry, the robotic arm, the subject support, and the like. The robotic control 22 controls the manipulator 18 or robotic arm to avoid collisions with the LINAC 6 and the LINAC beam during delivery of radiation. The robotic control positions the US probe to provide real-time 3D US images of the subject body regions which receive the radiation doses concurrently with the radiation delivery.

The LINAC 6 transmits beams of radiation into at least one targeted volume located in the subject body 4 based on a radiation therapy plan. Each beam of radiation is of a pre-determined size, shape, direction or orientation, strength, and duration and controlled by a LINAC control 28. The LINAC 6 moves about the subject body which is supported on the subject support 8. The subject support can move for alignment with the LINAC. The LINAC control can be embodied in the workstation 16 or a separate workstation, and operate as a console for the LINAC. The LINAC control 28 provides trajectory, shape, size, and other information concerning the radiation beams to the real-time 3D US unit 2.

The system includes an image registration unit 30 which receives a planning image 32, such as a CT, MR, PET, or SPECT image or combinations thereof from memory such as a storage management system, picture archiving and communication system (PACS), radiology information system (RIS), and the like, or directly from a scanner 34. The system includes a segmentation unit 35 which segments the targeted volumes and any OARs. For example, a tumor in the prostate is segmented as a targeted volume, and the prostate, bladder, and rectum of the subject are segmented as the OARs. The segmentation unit can identify the segmented structures superimposed in a display by the display device 12 of the real-time US images 3 or planning image. For example, the image with the targeted volume and OARs can include a color contrast of the boundaries of the targeted volume and/or a different color contrast of the boundaries of the OARs.

The image registration unit 30 deformably registers the segmented planning image 32 and 3D US baseline image 36. The baseline image 36 is acquired prior to delivery of the first fraction and can be reacquired and re-registered between fractions. The registration process generates deformation vectors 38 which are used to port tissue densities from the planning image based on the Hounsfield units, for example, and map the tissue densities to the baseline 3D US images stored in a memory as a 3D tissue map 40. The segmentations are also mapped to the 3D tissue map. In one embodiment, the segmented boundaries are mapped from the planning image to the 3D US baseline image. The various segmented regions can be each assigned a nominal density or other radiation attenuation factor for the tissue within each region.

During radiation treatment, a 3D US motion unit 42 registers each real-time 3D US image to the 3D tissue map using information from the tracking system 26 and image comparison with either the 3D US baseline image or the planning image directly. That is, the 3D tissue map is transformed into current shape and position of the target region and OARs. The motion measured can be due to respiratory motion, cardiac motion, patient movement, and single transient events such as coughing, sneezing, passing gas, etc.

A real-time dose engine 46 computes a real-time radiation dose delivered to the tissues based on the 3D tissue densities mapped to the real-time US images 3. The real-time dose engine includes in the computation the mapped tissue densities through which each beam of radiation passes. More specifically, the dose engine integrates the amount of radiation absorbed by each voxel of the registered 3D tissue map.

Transforming the targeted volumes and OARs of the tissue map to the current position and shape based on the motion identified by the 3D motion unit 44 enables the voxels along the radiation beam trajectory to be determined. Computing a real-time radiation dose accumulated for each voxel of the real-time 3D US images is based on the initial intensity of the radiation beam, the attenuation along the trajectory leading to and intersecting each voxel, and how much radiation is deposited in the time in the voxel for which the trajectory is intersecting the voxel. The deposited dose is integrated or summed over all the trajectories that intersect each voxel during the treatment as the treatment beams, the targeted region, and OARs move relative to their nominal position in the planning image. The cumulative dose map can optionally include a projected cumulative dose map based on the real-time dose computed and accumulated for each voxel and a projected value based on a remainder of a fractionated treatment planned from the RT treatment plan. The cumulative dose can be mapped and/or superimposed on the planning map.

The cumulative dose map 46 can be used by the system to modify the treatment process. The treatment process can be modified, for example, by terminating the process during a fraction when a planned dose is reached in a targeted volume and/or a maximum permitted threshold dose reaches an OAR. Alternatively, the treatment process can be modified by modifying one or more planned radiation beams remaining in the fractionated treatment. One or more radiation beams can be modified in size, shape, direction, strength, and/or duration. For example, a position of an aortic tumor shifts with breathing and cardiac rhythm, and a beam from a specific angle can be narrowed and/or gated during a particular rhythmic sequence to minimize exposure to heart tissues. In another example, a patient coughs and the radiation beam is temporarily gated until the targeted volume returns to position. In both examples, the real-time dose is computed throughout the process for even minor movements which leave the targeted volume in the center of the beam, but may move surrounding tissues. The cumulative dose can also be used to modify or recalculate future fractions.

The cumulative dose map 46 can be displayed on the display device 12 superimposed on the real-time 3D US images 3, baseline images 36, and/or the planning CT image 32. The cumulative dose map can be displayed as the cumulative dose or a projected cumulative dose. The cumulative dose map can be displayed as a difference between the cumulative dose map or projected cumulative dose map and the planned dose map from the RT treatment plan.

The various units or controls 2, 22, 28, 30, 42, 44, 46 are suitably embodied by an electronic data processing device, such as the electronic processor or electronic processing device 10 of the workstation 16, or by a network-based server computer operatively connected with the workstation 16 by a network, or so forth. Moreover, the disclosed imaging, registration, segmentation, mapping, control, and dose computation techniques are suitably implemented using a non-transitory storage medium storing instructions (e.g., software) readable by an electronic data processing device and executable by the electronic data processing device to perform the disclosed imaging, registration, segmentation, mapping, control, and dose computation techniques.

With reference to FIG. 2, one method of a real-time adaptive dose computation RT is flowcharted. The steps can be conceptually divided into steps before as part of RT planning and/or performed prior to delivery of radiation to the subject and steps performed during or as part of RT treatment. A RT plan is developed beginning with the acquisition of one or more 3D planning images 32 from the scanner 34 in a step 54. The planning image includes one or more targeted volumes for radiation therapy and typically includes OARs. The planning image is segmented and analyzed in a step 56 and the RT plan established which includes fractionated treatments. Each fractionated treatment includes a series of planned exposures to beams of radiation from the LINAC 6. Each beam of radiation is planned for size, shape, trajectory, strength, duration, and the like. The RT treatment plan is verified and recorded in a step 58. Verification can include simulation of the movement of the LINAC 6 and manipulator or robotic arm 18 of the real-time 3D US unit 2. The plan includes the control information used by the accelerator control 28 of the LINAC 6 and the robot control 22 of the US unit 2.

In a step 60, the baseline 3D US image 36 is acquired with the real-time 3D US imaging unit 2. The baseline image is acquired prior to the first fraction. The baseline image 36 is stored in a memory. The baseline can be re-acquired before each fractionated treatment. The acquired 3D US baseline image 36 is deformably registered with the segmented planning image 32 in a step 62 by the deformable image registration unit 30. The deformable registration process generates deformation vectors 38. If baseline images are re-acquired between fractionated treatments, then the re-acquired baseline images can be registered to the first acquired 3D US baseline image, to each other, and/or to the 3D CT planning image. The baseline image includes the tissues to which beams of radiation are to be delivered.

The tissue densities are ported, e.g. in Hounsfield units, from the planning image into the registered US baseline image in a step 64. The tissue densities are mapped to the registered 3D US baseline image based on the deformation vectors in a step 66. The 3D tissue map 40 and deformation vectors 38 are stored in a memory. The 3D tissue map 40 provides information for the attenuation of the beams of radiation.

The radiation is delivered to the tissues of the patient based on the RT treatment plan which includes beams of radiation of a size, shape, strength, duration, and orientation relative to the patient 4 supported on a patient support 8 in a step 68. The beams of radiation from the LINAC 6 are controlled by the accelerator control 28. Concurrently, in a step 70, the real-time 3D US imaging unit controlled by the robot control 22 acquires 3D real-time US images 3 of the tissues in the path of the radiation beam. The motion of the tissues are estimated in a step 68. The motion of the segmented targeted volumes and OARs are measured by the 3D motion unit 44. Each voxel of the 3D tissue map 40 is mapped to transform to its current location based on the real-time measured motion in a step 74.

The real-time dose computation engine 46 computes the real-time radiation dose delivered to the tissues based on the real-time 3D US images 3 and the 3D tissue density map 40 adjusted for motion in a step 72. The radiation beams from the LINAC 6 are tracked and measured relative to the real-time 3D US images 3. The real-time radiation dose is computed for each voxel of the real-time 3D US image. The real-time radiation dose is accumulated in the dose map 48 for the fractionated treatment. The real-time cumulative radiation dose 48 can include a projected dose for the remainder of the fractionated treatment. The real-time cumulative radiation dose 48 can be displayed by the display device superimposed on either of the 3D US real-time images 3 or the registered CT planning image 32. The computed real-time cumulative dose 48 can be displayed as a difference between the computed real-time cumulative dose 48 and the planned dose from the radiation therapy plan superimposed on either the CT planning image or the 3D US real-time images.

The RT delivery can be modified during the fractionated treatment based on the cumulative real-time dose map 48. The RT delivery can be modified by based on the measured motion. The RT delivery can be modified using the LINAC control 28 to modify real-time the size, shape, trajectory, strength, duration, etc. For example, the radiation beam parameters can be modified based on repetitive motion such as cardiac and/or respiratory motion. For example, the radiation beam parameters can be altered to accommodate the repetitive motion by changing the parameters of the radiation beam to move with the target, to temporarily turn on/off the beam as the target moves into or out of a defined range, change the size and/or shape of the beam as the targeted volume becomes less obscured by the OARs, etc. The beam parameters can be modified with motion due to events such as coughing, sneezing, or passing gas. For example, the radiation beams can be temporarily suspended until the targeted volume and/or OAR return to position, narrowed, and/or moved with the movement of the targeted area. The radiation beam parameter modification can include response(s) to the received positional and dosimetric information of the target and/or OARs, such as repositioning speeds of the LINAC, and/or patient movement such as controlled motion of the patient support to provide proper orientation of the radiation beam. The RT delivery can be modified to terminate when a threshold dose amount is reached in one or more targeted volumes and/or any OARs.

The cumulative real-time dose map 48 can be mapped to the original planning image for input into the next fractionated treatment planned using the step 56, adaptive radiation therapy planning It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A radiation therapy system, comprising:
   a real-time 3D imaging means for generating a baseline and a plurality of real-time 3D images of at least a portion of a subject body region including a target region and one or more Organs At Risk (OARs), the baseline image including an array of voxels with each voxel having a value indicative of radiation absorption properties of tissue in the voxel;
   a registration means for deformably registering a planning image of the subject body region and the baseline image, and mapping radiation absorptive properties of tissue in the planning image to the baseline image;
   a motion means for measuring motion of the target region and OARs during radiation therapy treatment based on the real-time 3D images; and
   a real-time dose computation means for computing a real-time radiation dose accumulated for each voxel of the real time 3D images based on an initial intensity of radiation beam, attenuation along a trajectory leading to and intersecting each voxel, and how much radiation is deposited in the voxel in a time which the trajectory is intersecting the voxel;
   wherein the radiation deposited is integrated or summed over all of trajectories intersecting each intersected voxel during the radiation therapy treatment as the radiation beams, the target region, and the OARs move relative to a nominal position in the planning image.

2. The system according to claim 1, wherein an amount of radiation deposited in each voxel of the planning image is assembled into an integrated dose map.

3. The system according to claim 2, further including:
   a radiation delivery means for delivering beams of radiation into the subject body region to intersect the target region, each beam of a size, shape, direction, strength, and duration based on a radiation treatment plan; and
   wherein the dose computation means controls the radiation delivery means to alter the radiation beams based on the integrated dose map.

4. A radiation system comprising:
   a diagnostic imaging system configured to generate 3D image data of at least a region of a subject body including a target and one or more Organs At Risk (OARs), the 3D image data being indicative of tissue density;
   a radiation source configured to deliver a beam of radiation at the target from a plurality of directions in each of a plurality of fractions in accordance with a radiation therapy plan during radiation treatment;
   an ultrasound transducer configured to generate real time 3D ultrasound image data of the region of the subject body; and
   one or more computer processors configured to:

reconstruct the 3D image data into a 3D planning image, the 3D planning image being indicative of tissue densities of each of a plurality of image voxels, segment the 3D planning image to identify the target and the OARs, reconstruct the 3D ultrasound image data in real time into 3D ultrasound images including a 3D baseline ultrasound image generated prior to radiation treatment, register the 3D planning image and the 3D baseline ultrasound image to provide voxels of the registered 3D baseline ultrasound image with tissue density information, deformably register the 3D baseline ultrasound image with the 3D real time ultrasound images, compute real-time radiation dose accumulated for each voxel of the real-time 3D ultrasound images based on an initial intensity of the radiation beam, an attenuation along each trajectory leading to and intersecting each voxel of the real-time 3D ultrasound image, and how much radiation is deposited in the voxel during a time which the trajectory is intersecting the voxel, and integrate or sum the deposited radiation over all trajectories that intersect each voxel during the treatment as the radiation beams, the target volume, and the OARs move relative to their nominal position in the planning image.

5. The system according to claim 4, wherein the one or more computer processors are further configured to:
compute a projected cumulative dose for a remainder of a current radiation therapy treatment fraction.

6. The system according to claim 4, wherein the one or more processors are further configured to:
control the radiation source to modify the radiation delivered based on the computed real-time cumulative dose.

7. The system according to claim 4, further including:
a robot configured to control position and/or orientation of the ultrasound transducer which generates the real-time 3D ultrasound image data.

8. The system according to claim 4, further including a display configured to display at least one of:
the 3D planning image,
an image of the real-time cumulative radiation dose, and
a superimposition image of the 3D planning image and the real-time cumulative radiation dose.

9. The system according to claim 1, further including:
a display means for displaying the computed real-time cumulative radiation dose superimposed on the 3D planning image.

10. The system according to claim 4, further including:
a display device which displays a difference between the computed real-time cumulative radiation dose and a planned radiation dose superimposed on the 3D planning image.

11. A method of radiation therapy, comprising:
with one or more processors, generating a 3D baseline image and a 3D planning image of a subject body region including a target and one or more Organs-At-Risk (OARs);
with the one or more processors, deformably registering the 3D planning image and the baseline 3D image;
with the one or more processors, mapping radiation absorptive properties of tissues in the subject body region from the 3D planning image to the baseline image;
with a radiation therapy device, delivering beams of radiation into tissue of the subject body region, each beam of a size, shape, direction, strength, and duration based on a radiation treatment plan;
measuring real-time motion of the target and organs at risk during radiation therapy treatment based on a series of real-time images;
with the one or more processors, mapping voxels of the 3D baseline image to a current position based on the measured real-time motion;
with the one or more processors, computing mapped tissue densities of voxels through which the beams of radiation pass;
with the one or more processors, computing attenuation along a radiation beam trajectory leading to and intersecting each voxel;
with the one or more processors, computing a real-time radiation dose accumulated for each voxel of the mapped baseline image based on an initial intensity of the radiation beam, the attenuation along the radiation beam trajectory leading to and intersecting each voxel, and how much radiation is deposited in each voxel during a time which the radiation beam trajectory is intersecting each voxel;
with the one or more processors, integrating or summing deposited radiation dose over all trajectories that intersect each voxel during the treatment as the radiation beams, the target region, and the OARs move relative to their nominal position in the 3D planning image; and
with the one or more processors, controlling the radiation therapy device to adjust at least one of the size, shape, direction, strength, and duration of the radiation beams to modify the radiation beams based on the computed accumulated real-time radiation dose.

12. The method according to claim 11, wherein the radiation treatment plan includes a plurality of fractions and further including:
computing a projected cumulative radiation dose for a remainder of a current fraction.

13. The method according to claim 11, further including:
with the one or more processors, controlling a display device to display cumulative radiation dose for each voxel superimposed on the planning image and/or real-time images.

14. A non-transitory computer-readable storage medium carrying software which controls one or more electronic data processing devices to perform the method according to claim 11.

15. A radiation therapy system, comprising:
a linear accelerator (LINAC) configured to deliver a plurality of beams of radiation into at least one targeted volume in a subject body, each beam of a size, shape, direction, strength, and duration based on a radiation treatment plan;
a robotic controlled ultrasound (US) imaging transducer configured to generate 3-dimensional (3-D) US image data of a region of the subject body which includes the at least one targeted volume, and surrounding tissues exposed to the plurality of beams of radiation;
at least one processor configured to:
repeatedly during delivery of the plurality of beams of radiation, reconstruct the US image data into 3-D images of the subject body which includes the at least one target volume and the surrounding tissue exposed to the plurality of beams of radiation;

deformably register a computed tomography (CT) x-ray planning image and a baseline one of the ultrasound (US) images generated prior to treatment, map tissue densities based on the CT x-ray planning image to the baseline US images to generate a 3D tissue density map;

measure motion of the target volume and surrounding tissues from the 3-D images generated during the delivery of the plurality of beams of radiation;

register the 3D tissue density map to the US images generated during the delivery of the plurality of beams of radiation;

compute a real-time radiation dose delivered to each voxel of the at least one targeted volume, organs at risk and surrounding tissues based on the 3D tissue density map;

wherein the 3D US images are generated during the delivery of the plurality of beams of radiation;

wherein the real-time radiation dose accumulated for each voxel is based on initial intensities of radiation beams leading to and intersecting each intersected voxel, attenuation along a trajectory of each of the plurality of beams of radiation, and how much radiation is deposited in a time the trajectory intersects each voxel;

integrate or sum the deposited dose over all the trajectories that intersect each voxel during the treatment as the plurality of beams of radiation, the at least one target volume, and OARs move relative to their nominal position in the CT x-ray planning image; and control the LINAC based on the computed real-time radiation dose and control a display to display the CT x-ray planning image in combination with the computed real-time radiation dose.

\* \* \* \* \*